United States Patent [19]
Tao et al.

[11] Patent Number: 6,046,332
[45] Date of Patent: Apr. 4, 2000

[54] METHODS FOR THE MANUFACTURE OF CETIRIZINE

[76] Inventors: Yong Tao, 175 Cedar Avenue, Apt. No. 501, Richmond Hill, Ontario, Canada, L4C 9V3; Khashayar Karimian, 18 Pine Cliff Drive, Mississauga, Ontario, Canada, L5N 3X1; Tim Fat Tam, 155 Veneto Drive, Woodbrige, Ontario, Canada, L4L 8X6

[21] Appl. No.: 09/214,714

[22] PCT Filed: Jul. 11, 1997

[86] PCT No.: PCT/CA97/00496

§ 371 Date: Jan. 20, 1999

§ 102(e) Date: Jan. 20, 1999

[87] PCT Pub. No.: WO98/02425

PCT Pub. Date: Jan. 22, 1998

[30] Foreign Application Priority Data

Jul. 11, 1996 [CA] Canada ................................. 2180993

[51] Int. Cl.[7] .............................................. C07D 241/04
[52] U.S. Cl. ............................................................ 544/396
[58] Field of Search ............................................. 544/396

[56] References Cited

FOREIGN PATENT DOCUMENTS

| | | |
|---|---|---|
| 568380 | 1/1959 | Canada . |
| 1199918 | 1/1986 | Canada . |
| 1317300 | 5/1993 | Canada . |
| 1320732 | 7/1993 | Canada . |
| 2 225 320 | 5/1990 | United Kingdom . |

OTHER PUBLICATIONS

E. Dorosec; D. Poljsak; U. Urleb: "Synthesis of N–Acylamino–ethoxyacetic Acid Derivatives" Archiv Der Pharmazie, vol. 325, No. 4, 1992, pp. 251–252.

Ligang Qian et al.: "A convenient Synthesis of Macrocyclic Lactams" Tetrahedron Lett., vol. 31, No. 45, 1990, pp. 6469–6472.

Jerry March: "Advanced Organic Chemistry" 1985, Wiley–Interscience, p. 1084—p. 1057–59.

*Primary Examiner*—Michael G. Ambrose
*Attorney, Agent, or Firm*—Nixon & Vanderhye P.C.

[57] ABSTRACT

The present invention relates to a process for the preparation of a [2-[4-[4-(chlorophenyl)phenylmethyl]-1-piperazinyl] ethoxy]acetic acid derivative of formula I:

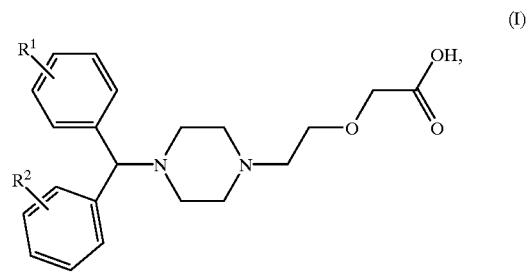

and, in particular, for the preparation of cetirizine. The method comprises the oxidation of a primary alcohol of a hydroxyzine. Cetirizine is a non-sedating type histamine H1-receptor antagonist and is used in the treatment of allergic syndromes.

6 Claims, No Drawings

METHODS FOR THE MANUFACTURE OF CETIRIZINE

FIELD OF THE INVENTION

The present invention relates to a new process for the manufacture of [2-[4-[4-(chlorophenyl)phenylmethyl]-1-piperazinyl]ethoxy]acetic acid derivatives of formula I and in particular for the manufacture of cetirizine.

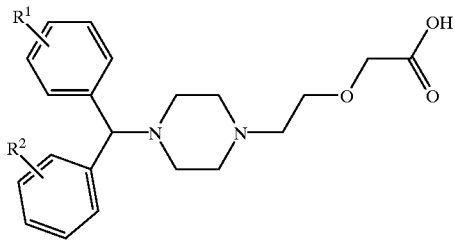

where
- $R^1$ and $R^2$ represent independently a hydrogen atom, a halogen atom, a lower alkoxy radical or a trifluoromethyl radical.

The term "lower alkoxy" as used herein means residues of both straight and branched chain aliphatic alcohols having from 1 to 4 carbon atoms, such as methoxy, ethoxy, butoxy and the like.

The halogen atom is Br, Cl, F, l.

BACKGROUND OF INVENTION

[2-[4-[4-(chlorophenyl)phenylmethyl]-1-piperazinyl] ethoxy]acetic acid also known by the generic name of cetirizine is a non-sedating type histamine H1-receptor antagonist and is used in the treatment of allergic syndromes. It's pharmacological and medicinal properties have been described in the literature, C. De. Vos et. Al., Ann. Allergy 59, 278, 1987; L. Juhlin et. Al, J. Allergy Clin. Immunol., 80, 80, 599 (1987).

Canadian Patent 1.199,918 describes the synthesis of cetirizine following two different routes as illustrated in Scheme 1:

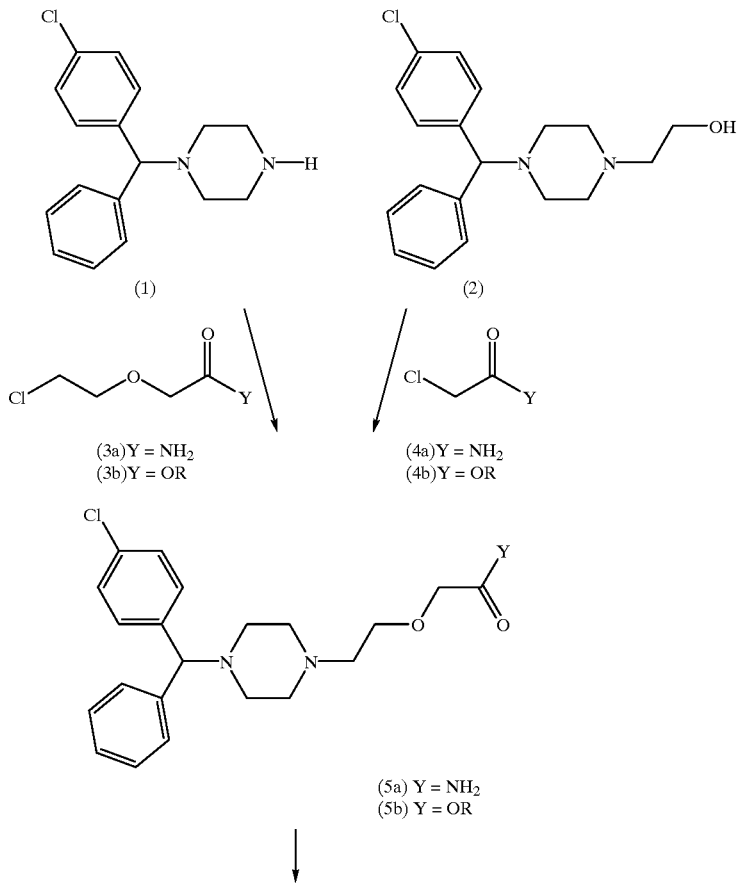

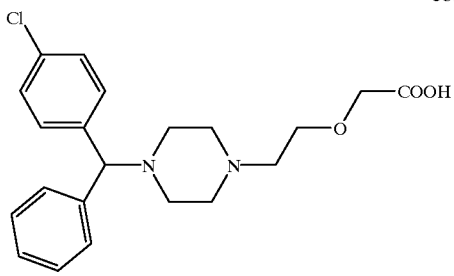

All the starting materials require for these 2 routes are not commercially available and accordingly these two routes involve a multi step process resulting in low overall yields.

Canadian Patent 1,317,300 teaches a process for preparing cetirizine by reaction of 1-[(4-chlorophenyl)phenylmethyl-piperazine with an haloethoxyacetonitrile. Again as all the starting materials are not commercially available and it results in a multi step process which generally is costly.

Canadian Patent 1,320,732 relates to a process for preparing cetirizine by reacting [2-[4-[4-(chlorophenyl)phenylmethyl]-1-piperazinyl]-ethanol with an alkali metal haloacetate. Again the starting alcohol results from a multi step process adding to the cost of the whole process and decreasing the overall yield.

There is a need to find an economical process for the production of these [2-[4-[4-(chlorophenyl)phenylmethyl]-1-piperazinyl]ethoxy]acetic acid derivatives which will allow for higher yields than those obtained in the prior art.

SUMMARY OF THE INVENTION

According to the present invention a process is provided for manufacture compounds of formula I:

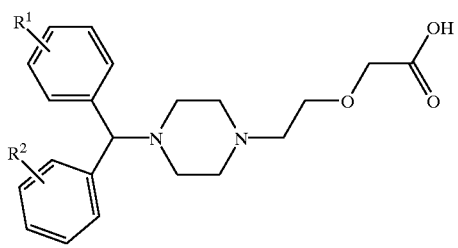

wherein $R^1$ and $R^2$ represent independently a hydrogen atom, a halogen atom, a lower alkoxy radical or trifluoromethyl radical.

The halogen atom is Br, Cl, F, I and preferably Cl which comprises reacting a compound of formula II:

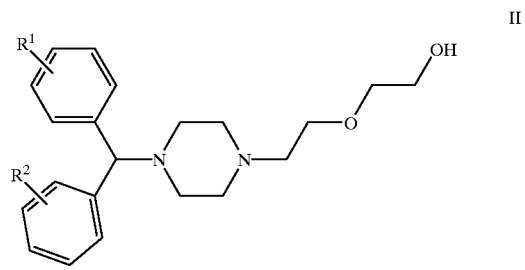

wherein
$R^1$ and $R^2$ are as defined above
with an oxidizing agent.

In another embodiment of the invention there is provided a process to prepare a compound of formula I where $R^2$=H and $R^1$=-parachloro by reacting hydroxyzine, a compound of formula II where $R^2$=H and $R^1$=-parachloro with an oxidizing agent as illustrated in Scheme 2:

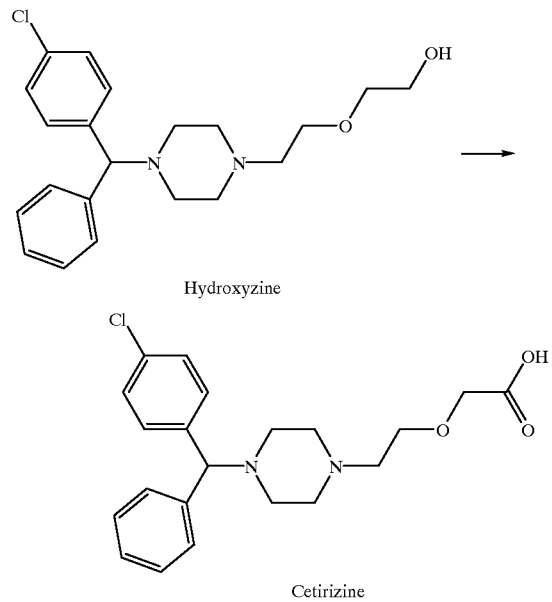

DETAILED DESCRIPTION OF THE INVENTION

The oxidation of the starting material of formula II takes place at room temperature in the presence of Jones reagent in acetone. Jones reagent is well known in the art and is prepared from chromium trioxide and sulphuric acid. As the oxidation of alcohols to carboxylic acids is well documented in the art, it would be obvious to any skilled reader that the oxidizing agent is not limited to Jones reagent but include many others, as for example platinum dioxide Pl/C with oxygen in the presence of an inert solvent.

Preferably the starting material of formula II used is hydroxyzine which is commercially available. Its synthesis was disclosed in Canadian Patent No. 568,380. The product of oxidation i.e. cetirizine is isolated by conventional means.

The present invention will be more fully understood by the following examples which illustrate the invention, but are not considered limiting the scope of the invention.

EXAMPLE 1

Preparation of [2-[4-[(4-chlorophenyl)phenylmethyl]-1-piperazinyl]-ethoxy]acetic acid (cetirizine).

To a stirred suspension of hydroxyzine dihydrochloride (70.0 g, 0.156 mol) in acetone (560 ml), Jones reagent (130 ml, 0.351 mol), which was made by adding sulphuric acid (115 ml) to a solution of chromium trioxide (133.7 g) in water (250 ml) and adding water to the total volume of 500 ml, was added dropwise in a period of 2 hours. The stirring was continued for further 17 hours at room temperature. Isopropanol (10 ml) was added dropwise and the mixture was stirred for 1 hour. 25% aqueous NaOH solution (250 ml) was added slowly to adjust pH to ca. 12. Celite (100 g) was then added and the suspension was stirred for 20 min. The mixture was filtered through a pad of celite (13×2 cm) and washed with 2:1 acetone-water (3×200 ml). Evaporation of the most acetone from the combined filtrate gave a aqueous suspension. The suspension was washed by ethyl acetate (100 ml) and 5% aqueous NaCl solution (100 ml) This washing procedure was repeated 5 times. Water (500 ml) was added to the isolated middle oily layer. 5% HCl aqueous solution was used to adjust pH to ca 2. After being washed with dichloromethane (2×200 ml), the aqueous solution was adjusted to pH=6 with 25% NaOH solution and extracted with dichloromethane (3×250 ml). The combined organic extract was treated with charcoal (10 g) and filtered through a pad of celite (13×2 cm). Evaporation of solvent afforded the titled compound as a pale white foam (36.8 g, yield 60%) $\delta_H$(CDCl$_3$; 300 MHz) 13.73 (1H, br), 7, 14–7.36 (9H, m), 4.24 (1H, s), 3.95 (2H, s), 3.68–3.78 (2H, m), 3.09 (4H, br), 2.89–2.98 (2H, m), 2.62 (4H, br); $\delta_C$(CDCl$_3$; 75.47 MHz) 175.09, 141.33, 140.53, 132.93, 128.95, 128.89, 128.83, 127.56, 74.65, 70.23, 66.56, 56.72, 53.09, 49.24; Found: M$^+$, 388.1544. C$_{21}$H$_{25}$Cl$_1$N$_2$O$_3$ requires M, 388.1554.

EXAMPLE 2

Preparation of [2-[4-[(4-chlorophenyl)phenylmethyl] 1-piperazinyl]-ethoxy] acetic acid (cetirizine).

To a stirred and heated (80° C.) suspension of hydroxyzine hydrochloride (1.0 g, 2.23 mmol) and 5% Pt/C in dioxane (10 mL) and 1N aqueous NaOH solution (10 mL), O$_2$ was bubbled through for 20 hours. After being cooled down to room temperature, The mixture was filtered through a pad of celite (2.5×2 cm) and washed with water. The filtrate was extracted with dichloromethane (3×25 mL). The combined organic solution was dried (Na2SO4). Evaporation of solvent gave the titled compound as a pale white form (0.51 g, yield 58.7%).

What is claimed is:

1. A process for preparing compounds of formula I:

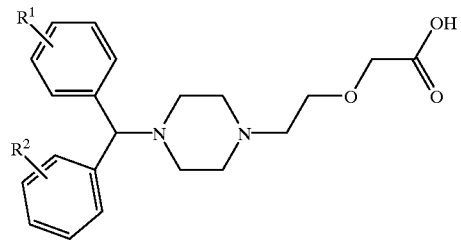

I wherein
R$^1$ and R$^2$ represent independently a hydrogen atom, a halogen atom, a lower alkoxy radical or a trifluoromethyl radical
which comprises reacting a compound of formula II:

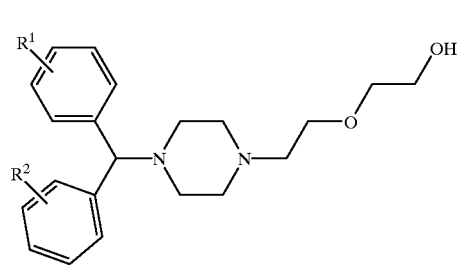

II wherein
R$^1$ and R$^2$ are as defined above
with an oxidizing agent.

2. A process according to claim 1 wherein the oxidizing agent is Jones reagent.

3. A process according to claim 1 wherein the oxidizing agent is platinum dioxide.

4. A process for preparing a compound of formula I:

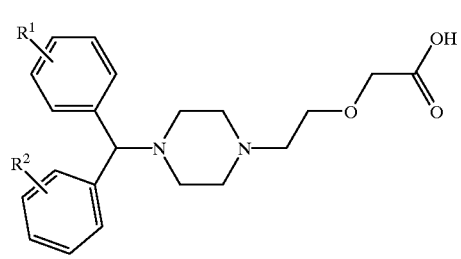

I where
R$^2$=H and R$^1$=-parachloro
which comprises reacting hydroxyzine with an oxidizing agent.

5. A process according to claim 4 wherein the oxidizing agent is Jones reagent.

6. A process according to claim 4 wherein the oxidizing agent is platinum dioxide.

* * * * *